United States Patent
Huang et al.

(10) Patent No.: US 8,057,531 B2
(45) Date of Patent: Nov. 15, 2011

(54) STENT HAVING CIRCUMFERENTIALLY DEFORMABLE STRUTS

(75) Inventors: Bin Huang, Dublin, CA (US); David C. Gale, Kennesaw, GA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 411 days.

(21) Appl. No.: 11/823,954

(22) Filed: Jun. 29, 2007

(65) Prior Publication Data

US 2009/0005854 A1 Jan. 1, 2009

(51) Int. Cl.
*A61F 2/06* (2006.01)
(52) U.S. Cl. ...................................... 623/1.15; 623/1.35
(58) Field of Classification Search ................. 623/1.15, 623/1.11, 1.24, 1.42; 424/423; 29/407.5
See application file for complete search history.

(56) References Cited

U.S. PATENT DOCUMENTS

| | | | |
|---|---|---|---|
| 5,108,416 A | 4/1992 | Ryan et al. | |
| 5,116,365 A | 5/1992 | Hillstead | |
| 5,139,480 A * | 8/1992 | Hickle et al. | 604/8 |
| 5,500,013 A | 3/1996 | Buscemi et al. | |
| 5,628,786 A | 5/1997 | Banas et al. | |
| 6,626,939 B1 | 9/2003 | Burnside et al. | |
| 2001/0044652 A1* | 11/2001 | Moore | 623/1.16 |
| 2003/0028246 A1 | 2/2003 | Palmaz et al. | |
| 2003/0083732 A1 | 5/2003 | Stinson | |
| 2003/0130718 A1 | 7/2003 | Palmas et al. | |
| 2004/0098090 A1 | 5/2004 | Williams et al. | |
| 2006/0025852 A1* | 2/2006 | Armstrong et al. | 623/1.17 |
| 2007/0293938 A1* | 12/2007 | Gale et al. | 623/1.15 |
| 2008/0132995 A1* | 6/2008 | Burgermeister et al. | 623/1.15 |

* cited by examiner

*Primary Examiner* — David Isabella
*Assistant Examiner* — Seema Swaminathan
(74) *Attorney, Agent, or Firm* — Squire Sanders & Dempsey (US) LLP (57) ABSTRACT

A method of treating a bodily lumen with a stent including disposing a stent within a bodily lumen in which the stent has a plurality of deformable struts that are substantially circumferentially aligned is described. The deformable struts are configured to selectively deform in a circumferential direction in localized regions in the struts upon application of an outward radial force. The stent is expanded by applying the outward radial force which causes selective deformation of the deformable struts in a localized region in the struts.

16 Claims, 4 Drawing Sheets

FIG. 3

STENT HAVING CIRCUMFERENTIALLY DEFORMABLE STRUTS

BACKGROUND OF THE INVENTION

1. Field of the Invention

Disclosed herein is a stent that is radially deformed in vivo after implantation of the stent in a bodily lumen.

2. Description of the State of the Art

This invention relates to radially expandable endoprostheses, which are adapted to be implanted in a bodily lumen. An "endoprosthesis" corresponds to an artificial stent that is placed inside the body. A "lumen" refers to a cavity of a tubular organ such as a blood vessel.

A stent is an example of such an endoprosthesis. Stents are generally cylindrically-shaped devices, which function to hold open and sometimes expand a segment of a blood vessel or other anatomical lumen. Stents are often used in the treatment of atherosclerotic stenosis in blood vessels. "Stenosis" refers to a narrowing or constriction of the cross-sectional area of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen. In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Additionally, the stent should also be longitudinally flexible to allow it to be maneuvered through a tortuous vascular path and to enable it to conform to a deployment site that may not be linear or may be subject to flexure. The material from which the stent is constructed must allow the stent to undergo expansion. Once expanded, the stent must maintain its size and shape throughout its service life despite the various forces that may come to bear on it, including the cyclic loading induced by the beating heart. Finally, the stent must be biocompatible so as not to trigger any adverse vascular responses.

The structure of a stent is typically composed of scaffolding that includes a pattern or network of interconnecting structural elements or struts. The scaffolding can be formed from wires, tubes, or sheets of material rolled into a cylindrical shape. The scaffolding is conventionally designed so that the stent can be radially contracted (to allow crimping) and radially expanded (to allow deployment). A conventional stent is allowed to expand and contract through movement of individual structural elements of a pattern with respect to each other. Such movement typically results in substantial deformation of localized portions of the stent's structure. The pattern of the stent is designed to maintain the longitudinal flexibility and radial rigidity required of the stent. Longitudinal flexibility facilitates delivery of the stent and radial rigidity is needed to hold open a bodily lumen.

A stent may be constructed of polymeric material. Polymeric stents require adequate circumferential strength and radial rigidity. Inadequate circumferential strength potentially contributes to a relatively high incidence of recoil of polymeric stents after implantation into vessels. The requirement of high strength and rigidity is seemingly at odds with the need for flexibility during delivery. The movable structural elements in the stent pattern provide some flexibility.

One potential problem with polymeric stents is that their struts can crack during crimping and expansion. The localized portions of the stent pattern subjected to substantial deformation tend to be the most vulnerable to failure. Therefore, it would be desirable to have a method of treating a bodily lumen with a polymeric stent in which the stent has adequate flexibility during delivery, high radial strength and rigidity after deployment, and that is relatively free of localized regions of high deformation susceptible to failure.

SUMMARY OF THE INVENTION

Disclosed herein is a method of treating a bodily lumen with a stent, the method comprising: disposing a stent within a bodily lumen, the stent comprising a plurality of deformable struts that are substantially circumferentially aligned and are configured to selectively deform in a circumferential direction in localized regions in the struts upon application of an outward radial force; and expanding the stent by applying the outward radial force, wherein the outward radial force causes selective deformation of the deformable struts in a localized region in the struts.

Also disclosed is a method of treating a bodily lumen with a stent, the method comprising: disposing a stent within a bodily lumen, the stent comprising a plurality of deformable struts having at least one recess, wherein the deformable struts are substantially circumferentially aligned and are configured to selectively deform in a circumferential direction in a localized region at or near the recesses in the struts upon application of an outward radial force; and expanding the stent by applying the outward radial force, wherein the outward radial force causes selective deformation of the deformable struts in the localized region in the struts.

Also disclosed is a stent comprising: a plurality of deformable struts that are substantially circumferentially aligned and are configured to selectively neck in a circumferential direction in a localized region in the struts upon application of an outward radial force, wherein deformable struts are of a semicrystalline polymer material having a glass transition temperature that is below 37° C. before necking.

DETAILED DESCRIPTION OF THE INVENTION

The term "stent" as used herein is intended to include, but is not limited to, balloon-expandable stents, stent-grafts, and vascular grafts. In general, stents are composed of a pattern or network of circumferential and longitudinally extending interconnecting structural elements or struts.

Processes to manufacture a stent may include extruding a polymeric tube for use in fabricating a stent. The polymer can be subjected to processing that enhances the mechanical strength of the polymer. The stent may then be crimped onto a delivery device to deliver the stent into a lumen for treatment. Due to radial expansion and the shape-memory of the polymers, polymer recoil may occur after the stent is deployed into the lumen. Crimping and expansion of a stent having a typical stent pattern result in regions of the stent experiencing high deformation during crimping and expansion. Thus, when a stent is crimped or expanded, some portions of a stent pattern may have no or relatively no strain, while others may have relatively high strain. Such strain on a stent may lead to cracking during crimping, sterilization, and expansion or deployment of the stent into the body lumen.

The embodiments disclosed herein provide for certain advantages regarding mechanical properties and stability. The deployment of the stent enhances the radial strength of the stent. Further, methods disclosed herein do not require the stent to be crimped to a smaller diameter in order to be delivered into a bodily lumen. Since the stent formed according to the embodiments described herein need not be crimped, the stent is less likely to suffer cracking during deployment.

Figure 1A:
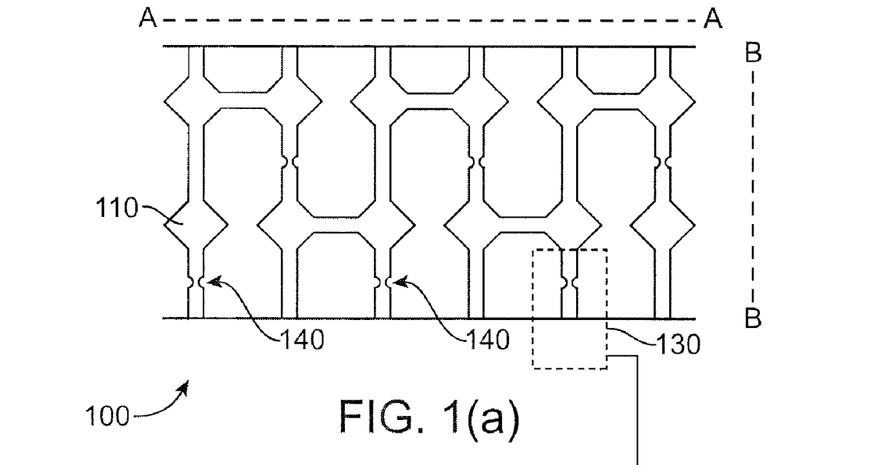
FIG. 1(a) depicts a stent having a plurality of deformable struts according to one embodiment of the invention.
Figure 1B:
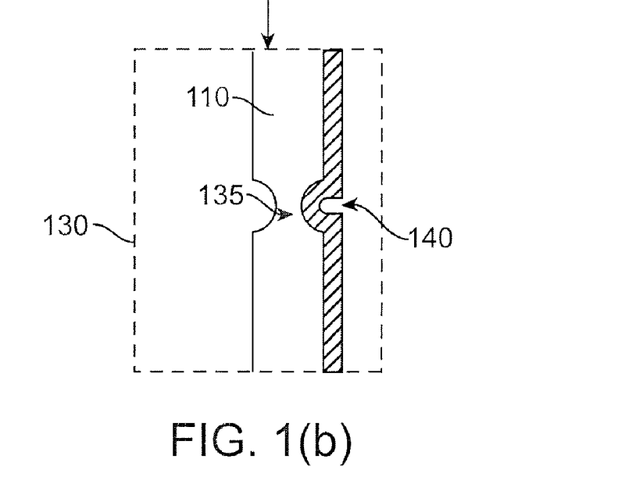
FIG. 1(b) depicts a close up view of a localized region having a deformable strut prior to deformation.

Embodiments provide for a polymeric stent having adequate flexibility during delivery as well as high radial strength and rigidity (high modulus) after deployment. The stent can also be made to be relatively free of localized regions of high deformation caused by bending struts that are susceptible to failure, which occurs when struts bend FIG. 1(a) depicts an axial projection of a stent 100 according to one embodiment of the invention having a plurality of deformable struts 110, with A-A corresponding to a longitudinal axis of the stent. As depicted, deformable struts 110 may be substantially aligned in a circumferential direction B-B. Thus, upon application of outward radial force, deformable struts 110 are configured to selectively deform or neck in direction B-B. Stent 100 is radially expanded to deploy in vivo by applying a radial force from a delivery implement, such as a balloon catheter. Stent 100 expands through selective deformation or necking of deformable struts 110 in localized regions 130 of struts 110. FIG. 1(b) depicts a close up view of a localized region 130 of strut 110 having a deformable region 135 and recess 140.

Figure 1C:
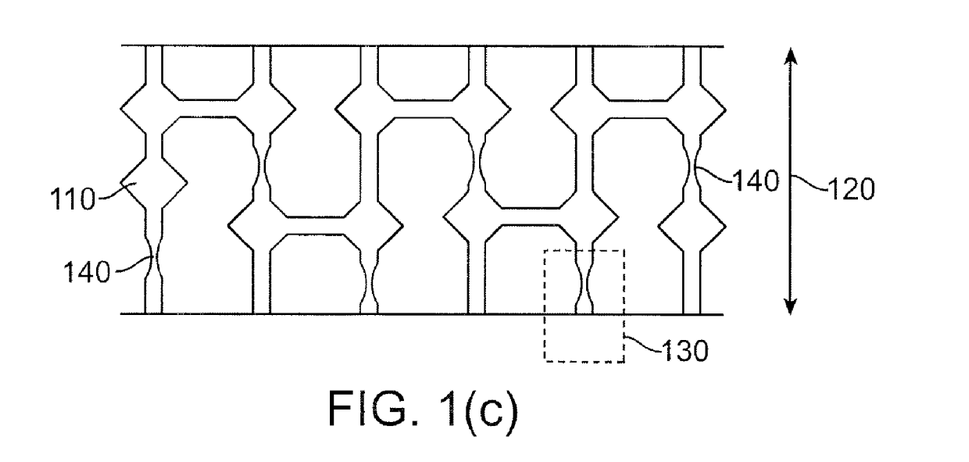
FIG. 1(c) depicts a stent having a plurality of deformed struts after deformation.
Figure 2A:
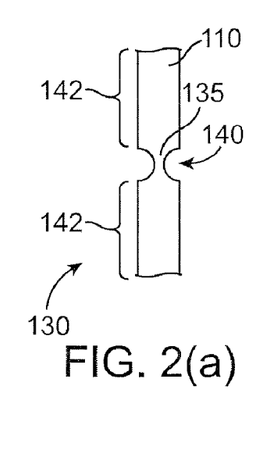
FIGS. 2(a)-(e) depict a deformable strut at various stages of selective deformation in a localized region.
Figure 2B:
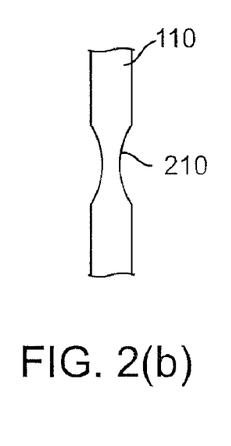
Figure 2C:
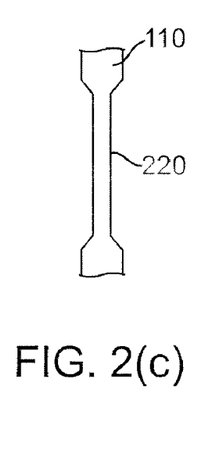
Figure 2D:
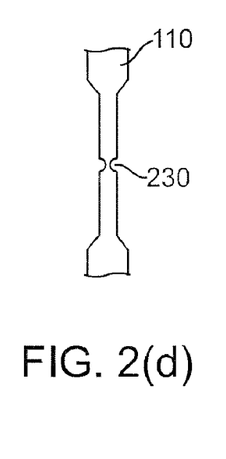
Figure 2E:
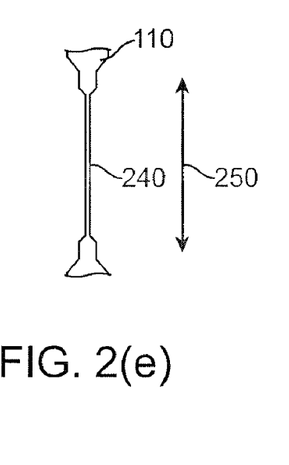

As outward radial force is applied, stress is applied to deformable struts 110 beyond the yield strength of the material, and necking occurs in deformable regions 135 as depicted in FIG. 1(c). "Stress" refers to force per unit area, as in the force acting through a small area within a plane. As a result of outward radial force on the stent 100, struts 110 are deformed along B-B causing stent 100 to be radially expanded.

In one embodiment, the deformable region 135 having a recess serves as an initial deforming point in deformable struts 110 and guides deformation in the circumferential direction 120 upon application of the outward radial force. As depicted, recess 140 can be formed by providing a region in deformable strut 110 having a smaller cross-sectional area than the remaining portion of deformable strut 110. Recess 140 may be formed, for example, by laser cutting the recess into the stent. The recess is not limited to the shape and size as depicted in FIGS. 1(a) and 1(b). Rather, recess 140 can be of any shape and size, so long as recess 140 is configured result in selective deformation or necking upon application of stress in deformable region 135 of recess 140. In general, the recess of the stent may have a smaller circumferential or lower mass. It is also contemplated that other features can serve as initial deforming points besides the use of a recess in the polymeric material, such as a notch or extension from the strut that initiates selective deformation. Also, struts 110 can include a polymeric region having a lower molecular weight as compared to other parts of the stent. Such regions can serve as initial deforming points in the deformable struts upon the application of radial force.

When the stent is deployed, an application of an outward radial force causes the stent to deform and radially expand. FIG. 1(c) depicts a stent having a plurality of deformed struts in the expanded condition. The outward radial force applied by a delivery implement causes deformable strut 110 to neck or elongate in localized regions 130 of the stent due to the recesses 140. As a result of the deformation of deformable struts 110, the entire stent 100 is radially expanded.

As depicted in FIG. 2, selective deformation upon application of radial force causes a deformed region 135 to deform resulting in a smaller cross-sectional area. Regions 142 on either side of recess 140 may experience deformation and decrease in cross-sectional area. Thus, in effect, deformable region 135 having recess 140 is elongated such that necking occurs in the polymeric material. Necking in deformable struts 110 in regions of struts with recesses 140 cause radial expansion or lengthening of deformable struts 110. Thus, recess 140 in deformable strut 110 serves as an initial deforming point that guides deformation as the stent is deformed circumferentially upon deployment. The substantially circumferentially aligned strut 110 having at least one recess 140 may be caused to deform upon expansion and deployment of a stent. Deformable strut 110 may be configured to deform at recess 140 upon application of radial force in the circumferential direction 250, causing necking of the polymeric material. Necking is induced in region 135 as depicted in FIG. 2(b), which causes deformed portion of region 135 to elongate to a longer deformed portion 220 upon further application of radial force. Eventually, a second deformed portion 230 is formed as depicted in FIG. 2(d). The second deformed portion 230 elongates upon further application of radial force as depicted in FIG. 2(e).

In one embodiment, the stent is expanded to a circumference that is two to six times its original circumference by expansion of the deformable struts. More narrowly, the stent is expanded to a circumference that is two to four times its original circumference by expansion of the deformable struts.

In one embodiment an outer diameter for a crimped stent is about 1.0 mm, and an outer diameter for the stent in the expanded state is about 3 mm.

Upon deformation of the deformable struts, the thickness of the deformed portions are reduced. After deployment, the tensile strength of the stent is also increased upon radial expansion of the stent during deployment.

The selectively deformed regions can exhibit an increase in crystallization and induced alignment of polymer chains along the circumferential direction. The crystals generated by circumferential deformation serve as an intrinsic locking mechanism. The induced crystallization and alignment increases the strength and the modulus along the deformation, or necked region. As a result, the radial strength and shape stability of the stent are increased.

Figure 3:
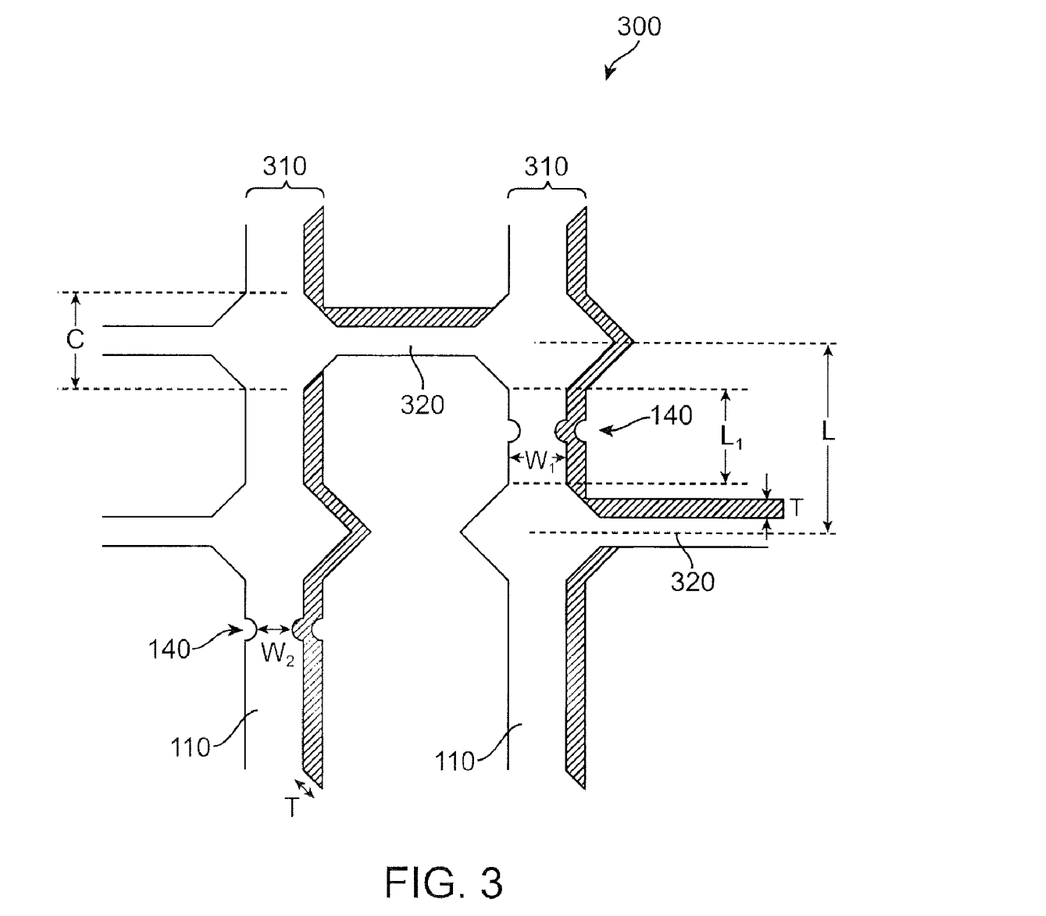
FIG. 3 depicts a close up view of a portion of the stent according to FIG. 1(a) having circumferential rings that include deformable struts and linking elements.

FIG. 3 depicts a close up view of a portion 300 of the stent according to FIG. 1(a) having circumferential rings 310 that include substantially circumferentially aligned, deformable struts 110 joined by linking struts 320. Deformable struts 110 having a length L, straight portions L1 of deformable struts, and linking struts 320 are depicted. Both struts 310 and 320 have a thickness T. Deformable strut length L, a length L1, and a wall thickness T of the linking elements 320 can be varied to obtain desired mechanical properties in the stent, such as radial strength and flexibility of the stent. Numerous embodiments are possible by varying the parameters of the stent. In addition, embodiments are not limited to the patterns depicted in FIG. 1.

FIG. 3 also illustrates that width of strut W2 at recess 140 which is smaller than the width W1 of the unrecessed portion of strut 110. In one embodiment, width W1 may be from about 0.010 to about 0.040 inches, more narrowly from about 0.020 to about 0.030 inches, or even more narrowly from about 0.022 to about 0.030 inches.

The width W2 at recess 140 may range from about 0.005 to about 0.009 inches, or more narrowly from about 0.005 to about 0.008 inches.

In one embodiment, wall thickness T may range from about 0.005 to about 0.009 inches, or more narrowly about 0.006 to about 0.008 inches.

Any number of parameters for the wall thickness T, strut width W2 at recess and strut width W1 at remaining portions of strut can vary.

The number of circumferential rings 310 around the circumference of the stent may also vary. In one embodiment, as depicted in FIG. 1(a), stent 100 has 6 circumferential rings.

By varying the length L of deformable strut, a desired radial expansion percentage may be achieved. Deformable strut length L describes the distance between the diamonds on the pattern. A connection section C describes the distance of the diamond-shaped connection section of the struts. In one embodiment, connection section C as depicted in FIG. 3 varies from about 0.008 inches to about 0.020 inches, more narrowly from about 0.010 inches to about 0.018 inches, and even more narrowly from about 0.011 inches to about 0.015 inches. These diamonds will stop deformation (expansion) of the strut. By adjusting the distance between the diamonds, it is possible to vary the amount of radial expansion allowed in the stent. In one embodiment, selective deformation causes a radial expansion of the stent to vary from 300% to 600% after deployment of the stent. It should be noted that the stent may encompass other designs not limited to the design depicted in FIG. 1 or FIG. 3.

Selective deformation of the deformable struts may induce crystallization and/or circumferential molecular orientation in the polymer. The polymer may crystallize during selective deformation to form crystals or net points that serve as intrinsic locking mechanisms that increase the mechanical property of the stent and stabilize the stent after radial expansion. In one embodiment, the selective deformation of the deformable struts increases the crystallinity in the polymer of the deformable struts to a crystallinity between about 10% to about 50%, more narrowly between about 20% to about 40%, and more narrowly between about 30% to about 40%.

As mentioned above, stents are conventionally radially expanded in order to impart mechanical properties in the stent to strengthen the stent. Such conventional methods also include crimping the radially expanded stent in order to deliver the stent into a bodily lumen before deployment into the lumen. In contrast, the embodiments disclosed herein provide for radial expansion in a bodily lumen by selective deformation in the lumen. Thus, mechanical properties are sufficiently imparted into the stent during deployment of the stent. Selective deformation of the deformable struts causes molecular orientation in the polymer and stabilizes the stent, thereby increasing mechanical strength of the deployed stent. In conventional stents, radial expansion is due to bending of curved portions of stents. Such stents are typically crimped from a fabricated diameter to a delivery diameter. Such bending portions are susceptible to cracking due to the crimping and expansion.

The stent need not be crimped prior to implantation. Since radial expansion is due to deformation of struts aligned in the circumferential direction, embodiments of the stent are fabricated at a delivery diameter. Thus, stent need not be crimped in order to deliver the stent into the lumen, but is rather implanted into the lumen in the unexpanded state as depicted in FIG. 1(a). Because the stent need not be crimped in order to deliver the stent into the lumen, the stent can be made to be free or relatively free of localized regions of high deformation caused by bending struts that are susceptible to failure.

Chemical and mechanical properties such as strength, modulus, and $T_g$ may be modified by inducing molecular orientation and crystallinity in the polymer. As mentioned above, the stent may be radially expanded and deployed in the bodily lumen. The stent is radially expanded by circumferentially deforming the deformable struts. Once expanded, the deformed struts expand the lumen and may support the lumen. The stent may be configured such that the deformable struts are expanded substantially uniformly around its circumference. Therefore, the radial strength and rigidity of the deformed struts may be increased by expansion or deployment of the stent in the lumen.

The degree of polymer chain alignment induced by stress upon deployment also depends on the temperature of the polymer when stress is applied to expand the stent. Below the $T_g$ of a polymer, polymer segments may not have sufficient energy to move past one another. Above $T_g$ of the polymer, polymer chain alignment may be readily induced with applied stress since rotation of polymer chains, and hence segmental mobility occurs relatively easily. Between $T_g$ and the melting temperature of the polymer, $T_m$, rotational barriers exist. However, the barriers are not great enough to substantially prevent segmental mobility. As the temperature of a polymer is increased above $T_g$, the energy barriers to rotation decrease and segmental mobility of polymer chains tends to increase. As a result, as the temperature increases, polymer chain alignment is more easily induced with applied stress.

In one embodiment, the polymer of the stent is near its $T_g$ during delivery of the stent. In some embodiments, the polymer of the stent has a $T_g$ at or below body temperature (37° C.), such that the stent is heated to the polymer's $T_g$ by inserting the stent into the body. Some embodiments may include heating the stent prior to delivering the stent into a body. Other embodiments may include heating the stent during delivery and/or during expansion of the stent.

After expansion in a lumen, it is generally desirable for a stent to remain rigid and maintain its expanded shape so that it may continue to hold open the lumen. In one embodiment, induced orientation and crystallization of the deformed regions of the struts after expansion or deployment of the stent increases the $T_g$ of at least a portion of the deformed struts. Thus, the $T_g$ of the polymer in the stent may be increased after expansion to above body temperature. Barriers to polymer chain mobility below $T_g$ inhibit or prevent loss of induced orientation and crystallization.

In one embodiment, the deformable struts include a semicrystalline polymeric material having a glass transition temperature that is below 37° C. before necking and above 37° C. after necking. In such an embodiment, the crystallinity of the deformable struts can be at least 30% after necking.

Additionally, it is desirable for a stent to have sufficient flexibility during delivery. Embodiments of the method described above allow a stent be flexible during delivery as well as be strong and rigid after deployment. The expansion of the stent and consequential necking that takes place during expansion of the stent which induces strength and rigidity is performed only after the stent is delivered to a desired location where it is expanded.

In some embodiments, the deformed struts are expanded plastically upon deployment, allowing the stent to retain its expanded shape upon deployment. In other embodiments, the deformed struts are elastically expanded. However, even an elastically expanded stent may retain its expanded shape if its temperature is below its $T_g$. Thus, applying stress-induced crystallization to the polymeric deformed strut may result in a permanently deformed high strength, high modulus material with a higher $T_g$ than the original polymeric strut prior to deformation. The term plastic deformation refers to permanent deformation that occurs in a material under stress after elastic limits have been exceeded. "Elastic limit" refers to the maximum stress that a material will withstand without permanent deformation.

To fabricate the stent, the tube is laser cut into a stent pattern that includes at least one recess in the plurality of substantially circumferentially aligned deformable struts. In one embodiment, a recess is included on every other circumferentially aligned strut. In another embodiment, a recess is included on every circumferentially aligned strut. In some embodiments, more then one recess is included on a circumferentially aligned strut. As mentioned above, the stent pattern may include any number of circumferentially aligned struts.

In one embodiment, the inner diameter of stent is slightly larger than a delivery implement's outer diameter to facilitate mounting the stent on the delivery device. In another embodiment, the inside cross-sectional area of the stent prior to expansion may be equal to an outside diameter of the delivery implement. The diameter of a stent is increased substantially or completely through circumferential deformation of the deformable struts rather than through changes in angles between structural elements.

A tube for use in fabricating the stent with desirable stent wall thickness may be extruded by a melt or solution process.

The stent may be coated with a drug, a polymer, or a polymer that includes a drug. The stent may be coated using any conventional stent coating method. The stent may be mounted on a delivery implement such as a balloon-catheter assembly. The delivery implement is capable of radially expanding the deformable struts in vivo.

The stent assembly may be sterilized by e-beam or other sterilization methods as known by those skilled in the art.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The polymer used to fabricate the stent can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

The stent may be fabricated from a blend of polymers. Representative examples of polymers that may be used to fabricate the stent or portions of the stent, such as the deformable struts include, but are not limited to, polymers selected from the group consisting of poly(glycolic acid), 90:10 poly (glycolic acid) and lactic acid, or mixtures thereof. Other polymers are also contemplated for use in fabricating the stent or portions of the stent, such as the deformable struts, will be discussed in detail below. In one embodiment, deformable struts include a polymer that is semicrystalline having a Tg in the range of 32° C. to 44° C. in the amorphous phase. The orientation that is imparted into the strut during deformation can increase the Tg of the deformed struts by up to 110° C. The increase in Tg of the deformed struts provides for implantation of a device having a Tg below body temperature at implantation of the device, and a Tg that is increased above body temperature during deployment of the device. In one embodiment, the modulus of a polymer can increase by 5 orders of magnitude as the polymer goes from below Tg to above Tg. As a result, a flexible, non-rigid material of the device turns into a more rigid material due to the expansion experienced during deployment of the device.

The $T_g$ of the blend may be tuned by adjusting the relative weight percent of the components in the blend. Representative examples of polymers for use in fabricating the deformable struts or other parts of the stent may include, but is not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of stents disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

EXAMPLES

For EXAMPLE 1, 2, and 3, a stent pattern having 6 circumferential rings as depicted in FIG. 1(a) was formed of a polymeric mixture of 90% glycolide and 10% poly L-lactide.

The width of the strut W1 was calculated based on mass balance.

Before expanded, the width of the strut W1=(length of straight portion L1*thickness T*strut width W1)=(0.0142 in*0.006 in*strut width W1).

After expanded, the width of the strut W1=(length of straight portion L1*thickness T*strut width at recess W2).

Therefore, the width of the strut W1=(0.006 in*0.006 in*0.050 in)/(0.006 in*0.0142 in)=0.0214 in. Using this value of the strut width, the strut design will be calculated to be (L1*T*W1), or (0.0142 in*0.006 in*0.0214 in).

Example 2

If the outer diameter of the stent was 0.048 inches, then the length of straight portion of deformable strut L1=[(Π*D)/6−0.012]=0.012 inches. To reach the end product target (deployed stent), W1−0.025 in. The stent strut design 0.012*0.006 in*0.025 in.

Example 3

A stent having a strut thickness W2 at recesses of 0.005 inches, a deployed inner diameter D of 3.5 mm, and a deployed outer diameter of 3.75 mm was formed.

$$L=(\Pi*D)/6=0.23\ in*\Pi=0.072\ in.$$

$$L1=0.072-0.0012=0.060\ in.$$

When the stent has an outer diameter of 0.046 in, L=(Π*D)/6=0.024 in. L1=(Π*D)/6 in−0.012=0.012 in.

The width of the strut W1 was calculated based on mass balance.

Before expanded, the width of the strut W1=(thickness T*length*strut width)=0.005*0.012*W1.

After expanded, the width of the strut W1=(thickness T*width W2*L1)=0.005*0.006*0.060. Thus, W1=0.03 in.

Therefore, the stent design was fabricated to be equal to the product of (0.005 in)(0.012 in)(0.030 in).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A method of treating a bodily lumen with a stent, the method comprising:
   disposing a stent within a bodily lumen,
   wherein the polymer stent comprises a plurality of circumferential rings composed of circumferentially aligned struts connected at the connection regions,
   wherein the connection region is diamond-shaped the circumferential rings connected by linking struts that connect adjacent rings at connection regions on the adjacent rings,
   wherein each ring has at least one deformable strut of the circumferentially aligned struts that has a region of reduced cross-section formed by a notch in a portion of the deformable strut between two connection regions,
   wherein the notched portion formed in the at least one deformable strut is for inducing necking in the deformable strut wherein the deformable struts are configured to selectively deform in a circumferential direction in localized regions in the deformable struts upon application of an outward radial force; and
   expanding the stent by applying the outward radial force, wherein the outward radial force causes selective deformation comprising necking in a circumferential direction of the deformable struts in the localized region in the struts,
   wherein the selective deformation is initiated at the reduced cross-section region,
   wherein the reduced cross-section region guides the necking in the circumferential direction.

2. The method according to claim 1, wherein selective deformation causes the cross-sectional area of the deformable struts adjacent to the notch to be decreased.

3. The method according to claim 1, wherein selective deformation induces crystallization and/or circumferential molecular orientation in the localized region of the deformable struts.

4. The method according to claim 1, wherein selective deformation increases a circumferential mechanical strength and/or modulus in the localized region of the deformable struts.

5. The method according to claim 1, wherein selective deformation increases the crystallinity in the polymer in the localized region of the deformable struts to at least 30%.

6. The method according to claim 1, wherein selective deformation increases the glass transition temperature of the polymer in the localized region of the deformable struts.

7. The method according to claim 1, wherein selective deformation increases the radial strength of the stent so that the stent is less likely to recoil.

8. The method according to claim 1, wherein selective deformation of the localized region includes lengthening of the deformable struts.

9. The method according to claim 1, wherein selective deformation includes plastic deformation of the deformable struts in the localized regions.

10. The method according to claim 1, wherein the deformable struts include a polymer that is semicrystalline having a Tg in the range of 32° C. to 44° C.

11. The method according to claim 1, wherein the deformable struts include a polymer that is selected from the group consisting of poly(glycolic acid), 90:10 poly(glycolic acid) and polylactide, or mixtures thereof.

12. The method according to claim 1, wherein the stent is expanded and deployed into the lumen after the temperature of the stent increases to body temperature.

13. The method according to claim 1, wherein only every other circumferentially aligned strut in each ring has the notch and only one of each longitudinally adjacent struts has the notch.

14. A polymer stent configured for being expanded by a balloon; comprising:
 a plurality of rings composed of struts connected at connection regions, wherein the connection region is diamond-shaped wherein all of the struts extend only in the circumferential direction, both before and after being expanded by the balloon;
 linking struts connecting adjacent rings at the connection regions;
 at least one deformable strut for each of the rings; and
 a notched portion formed in the at least one deformable strut to induce necking in the deformable strut, whereupon expansion of the stent the necking occurring at the notched portion enables the respective ring to increase in diameter and provide radial support for a bodily lumen.

15. The polymer stent of claim 14, wherein the notched portion is a pair of rounded notches formed on opposing sides of the at least one deformable strut and a narrow strut portion disposed between the rounded notches, wherein the narrow strut portion is configured to neck when the stent is expanded by the balloon.

16. The polymer stent of claim 15, wherein the distance between struts of adjacent rings is greater than the widths of the struts.

* * * * *